United States Patent [19]

Clough et al.

[11] 4,312,833

[45] Jan. 26, 1982

[54] STERILIZING HYDROPHILIC CONTACT LENSES

[75] Inventors: David Clough, Bishops Stortford; David J. Drain, Welwyn Garden City; Gary C. F. Ruder, Harlow, all of England

[73] Assignee: Smith & Nephew Pharmaceuticals, Ltd., England

[21] Appl. No.: 833,729

[22] Filed: Sep. 16, 1977

Related U.S. Application Data

[63] Continuation-in-part of Ser. No. 826,000, Aug. 19, 1977, abandoned, which is a continuation of Ser. No. 630,261, Nov. 10, 1975, abandoned.

[30] Foreign Application Priority Data

Nov. 14, 1974 [GB]  United Kingdom ............... 49354/74
Sep. 26, 1975 [GB]  United Kingdom ............... 39598/75

[51] Int. Cl.$^3$ .......................... A61L 2/16; A61L 2/18; C09K 3/00
[52] U.S. Cl. ............................... 422/30; 252/187 R; 252/188.3 R; 422/37; 424/14
[58] Field of Search ........ 21/58, 57, DIG. 3, DIG. 4; 252/187 R, 188.3 R; 424/14; 422/30, 37

[56] References Cited

U.S. PATENT DOCUMENTS

| | | | |
|---|---|---|---|
| 2,134,679 | 11/1938 | Allen | 21/58 |
| 2,668,763 | 2/1954 | Rubinstein | 252/187 R |
| 2,739,922 | 3/1956 | Shelanski | 252/187 R |
| 3,911,107 | 10/1975 | Krezanoski | 424/78 |

OTHER PUBLICATIONS

"Merck Index", 9th Ed., 1976, pp. 173 & 633.
Rose, "Condensed Chem. Dictionary", 7th Ed., 1966, pp. 863 & 864.

*Primary Examiner*—Bradley Garris
*Attorney, Agent, or Firm*—George W. Neuner; Robert L. Goldberg

[57] ABSTRACT

A sterilizing solution for contact lenses particularly those formed of a hydrophilic polymer comprises (a) an alkali metal salt of formic acid, and (b) an iodophor selected from the group consisting of complexes of iodine with hydrophilic polymer and non-ionic surface active agent. The alkali metal salt and the iodophor are present in predetermined quantities such that the sterilizing solution contains sufficient alkali metal salt to reduce the available iodine level of the sterilizing solution to substantially zero within a period of from 30 minutes to 8 hours at a temperature of from 20° to 25° C. The iodophor and the alkali metal salt of formic acid may be packaged in solid or powdered form, particularly in unit doses, and made into solution at the point of use.

45 Claims, No Drawings

STERILIZING HYDROPHILIC CONTACT LENSES

This application is a continuation-in-part of our pending application Ser. No. 826,000 filed Aug. 19, 1977 (now abandoned) which in turn is a continuation of application Ser. No. 630,261 filed Nov. 10, 1975 (now abandoned).

BACKGROUND OF THE INVENTION

This invention is concerned with improvements in and relating to the sterilization of articles.

The use of aqueous solutions containing available iodine for sterilizing articles is well established. Commonly, such sterilization is effected by contacting the article to be sterilized with the sterilizing solution, often by immersing the article therein. After removing the article from contact with the sterilizing solution it is often desirable to remove any adherent sterilizing solution from the article by, for example, rinsing with water, particularly when the article is to be brought into contact, directly or indirectly with human tissue.

SUMMARY OF THE INVENTION

It has now been found, in accordance with the present invention, that it is not necessary to remove adherent sterilizing solution provided that the sterilizing solution with which the article to be sterilized is brought into contact also contains a reducing agent capable of reducing the available iodine level of the sterilizing solution to substantially zero (with the production of non-toxic and non-irritant reaction products) in a period of at least 30 minutes at a temperature of from 20° to 25° C. Thus it has been found that the sterilizing capacity of effectiveness of a sterilizing solution containing available iodine as sterilizing agent is not adversely impaired by the presence of a reducing agent for reducing the level of available iodine provided that the reducing agent does not react with the iodine too fast, i.e. does not reduce the available iodine level to substantially zero in less than 30 minutes at a temperature of from 20° to 25° C. The reducing agent should be present in an amount to reduce substantially all of the available iodine and preferably the reducing agent and amount thereof should be such that substantially all of the available iodine is reduced within a period of not more than 8 hours at a temperature of from 20° to 25° C.

Accordingly, the present invention provides a method of sterilizing an article which comprises contacting the article with an aqueous solution of an iodophor containing sufficient organic reducing agent selected from the group consisting of reducing sugars, formic acid and alkali metal salts of formic acid, to reduce the available iodine level of the solution to substantially zero within a period of from 30 minutes to eight hours at a temperature of from 20° to 25° C.; the reaction products of the iodophor and the reducing agent being non-toxic and a non-irritant.

DESCRIPTION OF THE PREFERRED EMBODIMENTS

The term "iodophor" as used herein is intended to refer to a water-soluble complex of iodine with an organic complexing agent which complex, on solution in water, yields available (i.e. titratable) iodine. Suitable complexing agents include hydrophilic, water-soluble polymers such as cellulose ethers, polyvinylpyrrolidone and polyvinyl alcohol and anionic, cationic, nonionic and amphoteric surface active agents such as polyalkoxylated alkylphenols (e.g. nonylphenoxypoly (ethyleneoxy) ethanol), polyalkoxylated alkanols, long chain quaternary amines, alkyl sulphates (e.g. sodium lauryl sulphate) and alkylarylsulphonates (e.g. sodium alkylbenzene sulphonates). A particularly preferred iodophor for use in the method of the invention is a polyvinylpyrrolidone/iodine complex (so-called "Providone Iodine", hereinafter simply referred to as $PVP/I_2$ complex).

The iodophor should be present in the sterilizing solution in an amount sufficient to give a sterilizing level of available iodine bearing in mind the fact that the solution will also contain a reducing agent which will act to reduce the level of available iodine. In general, it has been found that provided the available iodine level is at least 5 ppm for a period of at least 15 minutes effective sterilization will be achieved. Accordingly, the iodophor will generally be present in the solution to give an initial available iodine level (i.e. the level of available iodine as determined by titration before the addition of or reaction with the reducing agent or contact with the article to be sterilized) of at least 10 ppm, preferably at least 20 ppm. The initial available iodine level will ordinarily not need to be above 300 ppm and is preferably from 25 to 100 ppm and most preferably is about 50 ppm.

As indicated above, the reducing agent employed in the method of the invention is an organic reducing agent selected from the group consisting of reducing sugars, formic acid and alkali metal salts of formic acid. Examples of reducing sugars for use in accordance with the invention include glucose and arabinose. For certain embodiments, as discussed more fully below, formic acid or an alkali metal salt thereof is the preferred reducing agent. A particularly preferred reducing agent is sodium formate. Such reducing agents reduce the available iodine to iodide ions and in the process are themselves converted to non-toxic and non-irritant products.

The initial sterilizing solution must contain the reducing agent sufficient to reduce the available iodine level of the solution to substantially zero (i.e. to 1 ppm or less, a level virtually undetectable by conventional analytical techniques) at commonly encountered ambient temperatures (e.g. 5°–40° C.). Accordingly the reducing agent must be present in molar excess of the available iodine. The actual molar excess of reducing agent will depend upon the nature of the iodophor and the reducing agent but generally it is preferred that the reducing agent be present in an at least tenfold molar amount relative to the available iodine in the iodophor, more preferably in an amount of from 10 to 800 moles per mole of available iodine, most preferably in an amount of from 100 to 500 moles per mole of available iodine.

As will be appreciated, in accordance with the method of the invention the article to be sterilized is immersed in the iodophor/reducing agent solution and allowed to remain immersed therein until the available iodine has been reduced to substantially zero (for example as indicated by the colour change of the solution from amber to colourless). The article may then be removed from the solution and if brought into direct or indirect contact with human tissue will have no undesirable toxic or irritant effects. Thus, the sterilizing method of the invention finds particular use in the sterilization of articles which are intended to come into contact with human tissue, e.g. surgical instruments and especially, contact lenses. The invention may also be applied to the sterilization of articles made of metal by the action of available iodine. In accordance with a preferred embodiment of the invention the sterilizing method is applied to contact lenses, especially so-called "soft" contact lenses or other articles made of similar hydrophilic polymers.

It is the common practice to store contact lenses made of hydrophobic polymers such as polymethylmethacrylate (so-called "hard lenses"), in water or saline when the lenses are not in use since, if they are not so stored, the lenses tend to undergo slight contraction or deformation since the polymers of which they are formed are not wholly hydrophobic and absorb small quantities of water. In the case of so-called "soft" contact lenses, i.e. those formed of hydrophilic polymers, namely lightly crosslinked polymers or copolymers of hydrophilic monomers such as hydroxyalkyl acrylates or methacrylates (e.g. hydroxyethyl methacrylate) or vinyl pyrrolidone, storage of the lens in water or saline when not in use is mandatory since such polymers when in use contain 20% or more of water (i.e. are in the form of "hydrogels") and hence undergo considerable deformation on drying. If allowed to dry out completely they become unacceptably brittle. It is most desirable that some degree of sterilization be effective whilst the lens is stored in the appropriate liquid in order that the lens may be maintained in an acceptably sterile condition for use. This may, in some cases, be achieved by heat sterilization of the liquid containing the lens but this is often unadvisable since some of the polymers are heat-sensitive, especially at sterilization temperatures. Accordingly, in the case of the "hard" lenses it has been the practice to incorporate bactericides in the storage liquid, commonly used bactericides being, for example, chlorhexidine and quaternary germicides such as benzalkonium chloride. Solutions containing these bactericides however, are inappropriate for the "soft" lenses since in the case of such polymers, the bactericide has been found to become preferentially concentrated within the hydrogel or polymer matrix. Accordingly, the lenses when removed from the storage solution can contain an unacceptably high concentration of bactericide which is subsequently eluted by the tear fluid when in position in the eye and may have a long or short term irritant effect.

The method of the invention may be applied to such "soft" contact lenses or articles made of similar hydrophilic polymers (hereinafter simply referred to as "lenses"). However, the polymers of the lenses are, as indicated above, in the form of hydrogels and contain substantial amounts of water. Accordingly the lenses themselves may absorb available iodine and it is therefore necessary to reduce (by means of the reducing agent) the iodine in the lenses to substantially zero for two reasons. Firstly, the presence of available iodine in the lens may cause a short or long term irritancy effect in the wearer's eye if the iodine is not substantially removed. Secondly, the lens on absorbing iodine acquires a yellowish/amber coloration and clearly the lens must be clear before being worn and hence the iodine must be substantially removed. The problem is exacerbated by the fact that it appears that in many cases the available iodine may preferentially concentrate in the lens as opposed to the sterilizing solution. In order for the reducing agent to reduce the iodine in the lens it appears that it is necessary for the reducing agent to pass from the sterilizing solution into the water contained in the lens hydrogel since otherwise an unduly long period of time (i.e. considerably in excess of eight hours) may be required to clear the lens of iodine. This is believed to be due to the fact that if the reducing agent cannot enter the lens hydrogel water it can only react with available iodine at the surface of the lens and that the iodine from the body of the lens is only slowly liberated at the lens surface. Accordingly the reducing agent employed in the sterilization of a lens should be one capable of entering the water of the lens hydrogel and not all reducing agents are apparently capable of so doing or if so are unduly irritant to the ocular tissue. However, it has been found that formic acid and its alkali metal salts (especially sodium formate) do meet the necessary criteria. Further, the iodophor (i.e. complexing agent) should be non-irritant to ocular tissue and it has been found that iodophors derived from hydrophilic polymers or nonionic surface active agents are not so irritant and are thus suitable for use in the sterilization of lenses.

Another factor which comes into consideration in the sterilization of lenses formed of hydrophilic polymers is the nature of the polymer itself. Thus such lenses are commonly derived from hydroxyl alkyl acrylates (e.g. hydroxyethyl methacrylate) and/or vinyl pyrrolidone as constituent monomers to provide the desired hydrophilic polymers. It has been found that polymers derived from monomers containing too great a proportion of vinyl pyrrolidone are very difficult to clear of iodine and, hence, it appears that the sterilizing method of the present invention is generally not suitable for the sterilization of polymers derived from more than 35% by weight of vinyl pyrrolidone, unless other modifying monomers, such as methacrylic acid, are present. It will in any event be a simple matter to establish, by simple test, whether any particular polymer may be satisfactorily sterilized using the method of the invention.

The pH of any residual liquid in contact with the soft lens should be from 5.0 to 8.0, preferably 6.5 to 7.5, and hence it is desirable that a pH adjuster, generally a buffer system, such as a phosphate buffer system be added to the sterilization solution, to bring the pH of the final liquid to the desired level. It has also been found that adjustment of pH to this level, especially to a level of about 7.1, markedly improves the effectiveness of some reagents.

It is also desirable that the tonicity of the final solution, after reaction with the reducing agent, be approximately equal to that of the eye fluids and, hence, it is also most desirable that a tonicity adjusting agent, generally sodium chloride, be added to the sterilization solution.

The buffers are suitably present in amounts to give from 100 to 10,000 ppm of buffer in the sterilization solution when used in the treatment of 50 ppm available iodine solutions. The tonicity adjusting agents should be present in the composition in an amount sufficient to render the solution approximately isotonic with human tears.

When calculating the amount of sterilizing agent buffering agent and/or tonicity adjusting to be present in the compositions of the invention, account must be taken of the strength of the iodine or iodine complex sterilization solution produced and the amount to be treated. A 50 ppm available iodine solution has been found to be very suitable for sterilizing soft contact lenses. Generally the lenses will be brought into contact with the sterilization solution in a so-called "lens case"

having a capacity of from 5–25 ml, preferably about 10 ml.

The sterilizing solution used in accordance with the invention will be prepared by dissolving the iodophor and reducing agent (and possibly tonicity adjusting agent and buffer) in water.

Considering only the iodophor and reducing agent the mixed solution may be prepared by:

(1) dissolving solid iodophor and solid reducing agent in water;

(2) mixing together individual preformed aqueous solutions of the reducing agent and iodophor;

(3) dissolving solid reducing agent in an aqueous solutions of iodophor, or (4) dissolving solid iodophor in a preformed aqueous solution of reducing agent.

In each case, the resulting solution (or in the case of methods (2), (3) and (4) the preformed solution or solutions) may be diluted with further water. However in all cases the amounts of iodophor and reducing agent and water (which may be solvent water where aqueous solutions of iodophor and/or reducing agent are employed) will, of course, be such as to provide a final sterilizing solution having the desired initial concentration of iodophor and reducing agent.

Accordingly it will be seen that in methods (1), (3) and (4) the iodophor and/or reducing agent may be added as a solid and for convenience of operation it is preferred that the solid iodophor and/or reducing agent be formulated in solid unit dosage form (e.g. a tablet) containing the appropriate amount of iodophor or reducing agent for addition to a predetermined amount of water (say for example about 10 ml in the case of a solution for sterilizing soft lenses in a lens case). It will be appreciated that in some cases it is not possible to formulate iodophors in solid form in which cases methods (1) and (4) will not be appropriate but solid iodophors are available (e.g. the $PVP/I_2$ complex) and thus may be used in these methods of operation. The solid unit dosage form may contain ingredients other than the iodophor or reducing agent and thus, in the case of the sterilization of soft lenses may contain buffering agents and/or tonicity adjusting agents. Further, in this latter case, the unit dosage form should not contain any insoluble excipient which will give rise to solid contaminants in the sterilizing solution which will adhere to the lens and then irritate the eye. This problem may be overcome by simply using sodium chloride (a tonicity adjusting agent) as excipient.

Iodophor-containing solid dosage unit forms for forming sterilizing solutions in accordance with the invention may contain from as little as 2 mg up to 5 g of iodophor, those intended for use in sterilizing contact lenses will generally contain from 2 to 30 mg, preferably from 2 to 10 mg, of iodophor whilst those intended for the more general sterilization of articles may contain from 200 mg to 2.5 g, preferably from 200 mg to 1,000 mg of iodophor, such a composition being suitable for addition to, say, 1 liter of water. In the case of sodium formate, for example, the corresponding reducing agent containing solid dosage unit forms suitably contains from 20 mg to 50 g of reducing agent, e.g. from 20 to 300, preferably from 20 to 100 mg of reducing agent in the case of those intended for use in sterilizing soft contact lenses.

In accordance with one particular embodiment of the present invention, it has been found that the iodophor and reducing agent may be put up together in a single solid dosage unit form which may subsequently be added to water to provide a sterilizing solution in accordance with method (1) above.

Accordingly, an embodiment of the present invention provides a solid dosage unit form comprising (a) a solid iodophor and (b) an organic reducing agent selected from the group consisting of reducing sugars and alkali metal salts of formic acid; components (a) and (b) being such that on dissolution in water the solid dosage unit form yields an aqueous solution of the iodophor containing sufficient of the organic aldehydic reducing agent to reduce the available iodine level of the solution to substantially zero within a period of from 30 minutes to 8 hours at a temperature of from 20° to 25° C.

These combined solid dosage unit forms will preferably contain the iodophor and reducing agent in the amounts set out above.

Such compositions are dry solid dosage units and may, thus, comprise tablets or a mixture of the dry constituents contained in a suitable container such as a hard or soft gelatine capsule. However, having regard to the fact that it is generally desirable that no extraneous, unwanted matter be introduced into a soft lens sterilizing solution it is preferred that the dosage unit form contain no extraneous material and thus it preferably takes the form of a solid tablet comprising only the active ingredients or, possibly, water-soluble non-irritant excipients such as boric acid or a polyethylene glycol. Such tablets may comprise a mixture of the active ingredients (iodophor and reducing agent) together with possible excipients or may take the form of two layer tablets, one layer comprising the iodophor and the other layer comprising the reducing agent. Alternatively the dosage unit forms of the invention for use in sterilizing soft contact lenses may comprise a two-part capsule (e.g. a two-part hard gelatine capsule) containing a mixture of the powdered ingredients, the user separating the two-parts of the capsule and introducing the powder into the water to be sterilized. This presentation has the advantage that no excipients are introduced into the sterilizing solution.

Methods (2), (3) and (4) also require the use of a preformed solution of iodophor or reducing agent. In these instances it should be noted that not all iodophors (e.g. $PVP/I_2$ complex) give stable solutions at the generally low (e.g. 50 ppm) available iodine concentrations envisaged in the practice of the invention and thus in the case of methods (2) and (3) the preformed iodophor solution may be a relatively concentrated solution (e.g. having a concentration of from 0.5 to 5% of available iodine) the bulk of the water content of the sterilizing solution being made up by the water of the reducing agent solution (method 2) or by adding water.

As indicated above, method (1) may be carried out using the solid iodophor/solid reducing agent dosage unit form referred to above. The invention also provides two-part packs for the practice of methods (1), (2), (3) and (4) and, thus provides two-part packs comprising:

(a) (i) a solid dosage unit form containing solid iodophor and solid reducing agent and (ii) water.

(b) (i) an aqueous solution of an iodophor and (ii) and aqueous solution of a reducing agent;

(c) (i) an aqueous solution of an iodophor and (ii) a solid dosage unit form containing a solid reducing agent;

(d) (i) an aqueous solution of a reducing agent and (ii) a solid dosage unit form containing a solid iodophor.

Two part pack (a) is suitable for carrying out method (1). Two part pack (b) will be suitable for carrying out method (2). Two-part pack (c) will be suitable for carrying out method (3). Two-part pack (d) will be suitable for carrying out method (4). In the case of packs (b) and (c) it may be desirable that the iodophor solution be in relatively concentrated form in which case additional water may be introduced by diluting the final solution or by using a relatively dilute solution of reducing agent in pack (b).

Methods (1) and (4) are currently the most preferred but it is to be understood that the invention is not limited thereto.

The solution (or water in the case of pack (a)) may be put up in individual containers (which may be sterilized in the case of the reducing agent solution) or in multidose containers, in which case a reducing agent solution may also contain a preservative bactericide, for example one also capable of reducing available iodine, e.g. glutaraldehyde or one which is chemically inert to iodine and is non-irritant and non-toxic, for example organic acids such as acetic acid, propionic acid or benzoic acid. When using such acids the final solution should be neutral and this may be achieved by introducing a buffering agent into the other component of the two-part pack. Where the sterilizing solution is intended for the sterilization of soft lenses the solution or solid may also contain a tonicity adjusting agent and/or buffering agent.

The dosage unit form may take any suitable form, preferably a dry solid form. However, having regard to the requirement that the composition leaves no insoluble particulate matter in the sterilization solution either as a result of the reaction or due to excipients (since this might irritate the eye) it is most convenient to simply tablet the ingredients without any excipient.

For sterilization of soft lenses the reducing agent solution should be sterile and, to this end may be made up in the form of sterilized (autoclavable) unit doses (e.g. containing about 10 ml of the solution) in suitable autoclavable containers such as bottles or plastics laminated foil sachets with low moisture vapour pearmeability, or in the form of a multidose composition to be contained in a suitable container and also containing a sterilizing or antibacterial agent. Such an antibacterial agent should be one which does not concentrate in soft hydrophilic polymers and most preferably is one which does not react with iodine, e.g. benzoic acid.

In order that the invention may be well understood the following Examples are given by way of illustration only.

EXAMPLE 1

PVP/$I_2$ tablets for addition to 10 ml sachets of sodium formate solution had the following composition.

| PVP/$I_2$ | 5 mg/tablet |
| Sodium chloride | 35 mg/tablet |
| Boric acid | 1.25 mg/tablet |

The PVP/$I_2$ and sodium chloride were each passed through a 60 mesh sieve and then mixed together. Boric acid (passing through an 80 mesh sieve) was added to the mixture as lubricant. The mixed powders were tabletted using 5/32 inch punches and dies.

The sodium formate solution had the following composition:

| Sodium formate | 0.5% by weight |
| Sodium dihydrogen phosphate | 0.023% by weight |
| Disodium hydrogen phosphate | 0.100% by weight |
| Distilled Water | 100% by weight |

The solution was prepared by dissolving the salts in water and was then put up in 10 ml lots in polypropylene/aluminium/nylon sachets which were then sterilized by autoclaving. The pH of the bulk solution was 7.3, that of the sterilized solution 7.3 and that of the spent solution (i.e. one obtained by reaction with a PVP/$I_2$ tablet) was 7.1.

EXAMPLE 2

Sodium formate tablets for addition to 10 ml lots of 50 ppm PVP/$I_2$ solution had the following composition:

| Sodium formate | 50 mg/tablet |
| Sodium dihydrogen phosphate | 2.3 mg/tablet |
| Disodium hydrogen phosphate | 10 mg/tablet |
| Boric acid | 2.5 mg/tablet |
| Sodium chloride | 35.2 mg/tablet |

The tablets were prepared by mixing the powdered ingredients and tabletting the mixed powders using 3/16 inch punches.

The PVP/$I_2$ solution for use with the above tablets is made up by adding 0.05 ml of a 1% available iodine aqueous solution of PVP/$I_2$ (e.g. from a dropper) to 10 ml of distilled water (e.g. contained in a lens case).

EXAMPLE 3

An aqueous sterilization solution is made up by adding 0.05 ml of a 1% available iodine aqueous solution of PVP/$I_2$ to 10 ml of the sodium formate solution of Example 1.

EXAMPLE 4

Tablets having the formulation given below are prepared as follows.

| PVP/$I_2$ | 5 mg per tablet |
| Sodium formate | 50 mg per tablet |
| Sodium chloride | 29.8 mg per tablet |
| Boric acid | 13.5 mg per tablet |
| Total | 98.3 |

PVP/$I_2$ complex powder is sieved through a No. 60 sieve and dried at 60° C. overnight.

Sodium formate and sodium chloride are dried at 60° C. and then sieved, the material passing through a No. 40 sieve but being retained on a No. 60 sieve being retained for use.

Appropriate quantities of the dried and sieved PVP/$I_2$ complex, sodium formate and sodium chloride are mixed together and finely powdered boric acid is added to the mixture as lubricant. The mixture is then tabletted using ¼ inch punches.

These tablets are suitable for use with 10 ml lots of solution having the following formulation:

| Anhydrous sodium dihydrogen phosphate | | 0.023% |
| Anhydrous disodium hydrogen phosphate | | 0.100% |
| Distilled water | ad | 100.000% |

This solution is packed as 10 ml lots into single dose containers (metal foil/plastic sachets) and sterilized.

A solution suitable for the sterilization of soft contact lenses is prepared by adding one of the above tablets to one 10 ml lot of the solution. It will be seen that in this example the tonicity adjusting agent (sodium chloride) is included in the solid dosage form and the buffering agent in the water.

EXAMPLE 5

Tablets having the following formulation are made

| | |
|---|---|
| PVP/$I_2$ | 5 mg per tablet |
| Sodium formate | 50 mg per tablet |
| Sodium chloride | 30 mg per tablet |
| Boric acid | 8.5 mg per tablet |

These tablets may be used with 10 ml lots of the aqueous solution described in Example 4 in the manner described in Example 4.

EXAMPLE 6

Tablets having the following formulation are made.

| | |
|---|---|
| PVP/$I_2$ | 5.0 mg per tablet |
| Sodium formate | 50.0 mg per tablet |
| Sodium dihydrogen phosphate | 2.3 mg per tablet |
| Disodium hydrogen phosphate | 10.0 mg per tablet |
| Sodium chloride | 30.0 mg per tablet |
| Boric acid | 8.5 mg per tablet |

These tablets are suitable for use in the sterilization of soft lenses by addition of one tablet to 10 ml of sterile distilled water.

EXAMPLES 7–9

Two-part hard gelatine capsules are filled with the powdered ingredients listed in the table below.

| | Amounts of component in mg per capsule EXAMPLE | | |
|---|---|---|---|
| Component | 7 | 8 | 9 |
| PVP/$I_2$ complex | 5 | 5 | 5 |
| Sodium formate | 50 | 50 | 50 |
| Sodium chloride | 29.8 | 30.0 | 30.8 |
| Sodium dihydrogen phosphate | — | — | 2.3 |
| Disodium hydrogen phosphate | — | — | 10.0 |

The capsules of Examples 7 and 8 may be used with 10 ml lots of the sterile buffered solution described in Example 1 and the capsule of Example 9 with 10 ml lots of sterile distilled water.

EXAMPLE 10

Use of Multidose Formate Solution Containing Preservative

| Solution | |
|---|---|
| Sodium Formate | 0.5% |
| Benzoic Acid | 0.079% |

| | |
|---|---|
| Distilled Water ad | 100.000% |
| (This solution has a pH of approx 4.6) | |
| Tablet | |
| PCP/$I_2$ | 5.0 mg per tablet |
| Disodium hydrogen phosphate | 10.0 mg per tablet |
| Sodium carbonate anhydrous | 4.5 mg per tablet |
| Sodium chloride | 28.0 mg per tablet |
| Sodium benzoate | 3.0 mg per tablet |

When 1 tablet is reacted with 10 ml of the above solution, the resulting solution is is isotonic and has a pH of approximately 7.1.

The sterilizing activity of the combined tablets and solution of Example 1 was tested by preparing a test solution from two tablets and two sachets to give a total volume of test solution of 20 ml. This volume of solution was employed since the test procedure required removal of 2 ml aliquot at periodic intervals.

The solution was tested individually for activity against the following organisms:

| | |
|---|---|
| *Staphylococcus aureus* | NCTC 6571 |
| *Pseudomonas aeruginosa* | NCTC 6780 |
| *Escherischia coli* | NCTC 86, and |
| *Candida Albicans* | |

The tests were carried by adding, to 20 ml of the test solution, 0.2 ml lots containing $10^5$–$10^6$ organism/ml of the organism by the addition of 0.2 ml of a standardised solution of the organism in 0.25 strength Ringer solution.

The inoculated solutions were maintained at 24°–26° C. and 2 ml aliquots removed at 1 minute after addition of the test organism and 15 minutes after addition of the test organism.

The aliquots (in 2×1 ml lots) were transferred to 18 ml of Neutralizing medium and then incubated at 37° C. for 40 hours to establish the presence or absence of organisms.

In a similar set of tests the formate solution was replaced by a solution containing the buffer only.

The results are shown in the following Table.

| | Time (mins) to sterilize solution | |
|---|---|---|
| Test organisms | PVPI$_1$/Formate | PVPI$_2$/Buffer |
| S. aureus | 15 | 15 |
| P. acruginosa | 15 | 15 |
| E. coli | 15 | 15 |
| C. Albicans | <1 | <1 |

The above tests were repeated except that a pair of soft contact lenses (hereinafter referred to as lenses A and B) were present in the solution. The results obtained were substantially the same. Lens A was formed of poly(hydroxyethyl methacrylate) cross-linked with 0.27–0.3% of ethylene glycol dimethacrylate. Lens B was formed of a copolymer of 2-hydroxy-1-methoxyprop-3-yl methacrylate vinyl pyrrolidone and methyl methacrylate containing 30% of vinyl pyrrolidone.

A number of experiments were carried out to investigate the rate of decomposition of iodophor solutions using various reducing agents. The results are summarised in the following table.

Time (to nearest 5 minutes)

-continued

| Experiment No. | Iodophor (initial concentration ppm) | Reducing Agent (concentration % w/v) | Temp. °C. | Other Ingredients present in solute (concentration % v/w) | | 50% of original level | 25% of original level | substantially zero |
|---|---|---|---|---|---|---|---|---|
| 1 | PVP/$I_2$ (25) | sodium formate (0.5%) | 20 | $NaH_2PO_4$<br>$Na_2HPO_4$<br>Boric acid<br>NaCl | (0.023)<br>(0.10)<br>(0.025)<br>(0.352) | 10 | 25 | 50 |
| 2 | PVP/$I_2$ (50) | sodium formate (0.5%) | 20 | $NaH_2PO_4$<br>$Na_2HPO_4$<br>Boric acid<br>NaCl | (0.023)<br>(0.10)<br>(0.025)<br>(0.352) | 20 | 40 | 75 |
| 3 | PVP/$I_2$ (58) | sodium formate (0.3) | 25 | $Na_2HPO_4$<br>$NaH_2PO_4$<br>$H_3BO_3$<br>NaCl | (0.14)<br>(0.06)<br>(0.011)<br>(0.714) | 40 | 70 | 130 |
| 4 | " | sodium formate (0.4) | 25 | $Na_2HPO_4$<br>$NaH_2PO_4$<br>$H_3BO_3$<br>NaCl | (0.14)<br>(0.06)<br>(0.011)<br>(0.714) | 35 | 60 | 110 |
| 5 | " | sodium formate (0.5) | " | $Na_2HPO_4$<br>$NaH_2PO_4$<br>$H_3BO_3$<br>NaCl | (0.14)<br>(0.06)<br>(0.011)<br>(0.714) | 30 | 50 | 95 |
| 6 | PVP/$I_2$ (610) | Sodium formate (0.5) | " | $NaH_2PO_4$<br>$Na_2HPO_4$ | (0.2) | >200 | — | >8 hours (estimated) |

| Experiment No. | Iodophor (initial concentration ppm) | Reducing Agent (concentration % w/v) | Temp. (°C.) | Other Ingredients present in solute (concentration % w/v) | | 50% of original level | 25% of orginal level | substantially zero |
|---|---|---|---|---|---|---|---|---|
| 7 | PVP/$I_2$ (330) | sodium formate (0.5) | 25 | $NaH_2PO_4$<br>$Na_2HPO_4$ | (0.2) | 185 | — | >7 hours (estimated) |
| 8 | PVP/$I_2$ (127) | sodium formate (0.5) | " | $NaH_2PO_4$<br>$Na_2HPO_4$ | (0.2) | 45 | 110 | 6 hours (estimated) |
| 9 | PVP/$I_2$ (51.5) | sodium formate (0.5) | " | $NaH_2PO_4$<br>$Na_2HPO_4$ | (0.2) | 25 | 40 | 90 |
| 10 | PVP/$I_2$ (25) | D-glucose (0.16) | " | $NaH_2PO_4$<br>$Na_2HPO_4$ | (0.2)<br>(pH 6.5) | 75 | 190 | Ca. 8 hours (estimated) |
| 11 | " | D-glucose (0.43) | " | $NaH_2PO_4$<br>$Na_2HPO_4$ | (0.2)<br>(pH 6.5) | 25 | 50 | 125 |
| 12 | " | D-glucose (0.8) | " | $NaH_2PO_4$<br>$Na_2HPO_4$ | (0.2)<br>(pH 6.5) | 15 | 35 | 75 |
| 13 | PVP/$I_2$ (25) | Arabinose (0.8) | 25 | $NaH_2PO_4$<br>$Na_2HPO_4$<br>KBr<br>NaCl<br>$H_3BO_3$ | (0.05)<br>(0.625)<br>(0.006)<br>(0.611)<br>(0.834) | 65 | 120 | Ca. 6 hours (estimated) |
| 14 | PVP/$I_2$ (25) | D-glucose (0.8) | 25 | $NaH_2PO_4$<br>$Na_2HPO_4$<br>KBr<br>NaCl<br>$H_3BO_3$ | (0.05)<br>(0.625)<br>(0.006)<br>(0.611)<br>(0.834) | 85 | 165 | Ca 8 hours (estimated) |
| 15 | " | Maltose (0.8) | " | $NaH_2PO_4$<br>$Na_2HPO_4$<br>KBr<br>NaCl<br>$H_3BO_3$ | (0.05)<br>(0.625)<br>(0.006)<br>(0.611)<br>(0.834) | 160 | Ca. 5.5 hours (estimated) | Ca. 10 hours (estimated) |
| 16 | " | Lactose (0.8) | " | $NaH_2PO_4$<br>$Na_2HPO_4$<br>KBr<br>NaCl<br>$H_3BO_3$ | (0.05)<br>(0.625)<br>(0.006)<br>(0.611)<br>(0.834) | 175 | Ca. 6 hours (estimated) | Ca. 10 hours (estimated) |
| 17 | " | D-glucose (0.16) | 20 | $NaH_2PO_4$<br>$NaHPO_4$ | (0.2)<br>(pH-7.1) | 60 | 105 | 210 |
| 18 | " | D-glucose (0.32) | " | $NaH_2PO_4$<br>$NaHPO_4$ | (0.2)<br>(pH-7.1) | 25 | 45 | 85 |
| 19 | " | D-glucose | " | $NaH_2PO_4$ | (0.2) | 20 | 30 | 65 |

-continued

| | | | | NaHPO₄ | (pH-7.1) | | | |
|---|---|---|---|---|---|---|---|---|
| 20 | " | D-glucose (0.80) | " | NaH₂PO₄ | (0.2) | 15 | 20 | 40 |
| | | | | NaHPO₄ | (pH-7.1) | | | |

| Experiment No. | Iodophor (initial concentration of $I_2$, ppm by titration) | Reducing Agent (concentration % w/v) | Temp (°C.) | Other ingredients present in solute (concentration % w/v) | | Time (to nearest 5 minutes) taken to reduce initial available iodine concentration to | | |
|---|---|---|---|---|---|---|---|---|
| | | | | | | 50% of original level | 25% of original level | substantially zero |
| 21 (1) | Complex of Iodine + sodium lauyl sulphate (50) | Sodium formate (0.5) | 220 | NaH₂PO₄<br>Na₂HPO₄<br>Boric acid<br>NaCl | (0.023)<br>(0.10)<br>(0.025)<br>(0.352) | 35 | 60 | 120 |
| 22 (2) | Antorax (50) | Sodium formate (0.5) | " | NaH₂PO₄<br>Na₂HPO₄<br>Boric acid<br>NaCl | (0.023)<br>(0.10)<br>(0.025)<br>(0.352) | 10 | 25 | 60 |
| 23 (3) | Antorax (50) | Sodium formate (0.5) | " | NaH₂PO₄<br>Na₂HPO₄<br>Boric acid<br>NaCl | (0.023)<br>(0.10)<br>(0.025)<br>(0.352) | 20 | 40 | 120 |
| 24 (4) | Antorax (50) | Sodium formate (0.5) | " | NaH₂PO₄<br>Na₂HPO₄<br>Boric acid<br>NaCl | (0.023)<br>(0.10)<br>(0.025)<br>(0.352) | 20 | 45 | 120 |
| 25 (5) | Antorax (50) | Sodium formate (0.5) | " | NaH₂PO₄<br>Na₂HPO₄<br>Boric acid<br>NaCl | (0.023)<br>(0.10)<br>(0.025)<br>(0.352) | 20 | 55 | 180 |
| 26 (6) | Wescodyne (50) | Sodium formate (0.5) | " | NaH₂PO₄<br>Na₂HPO₄<br>Boric acid<br>NaCl | (0.023)<br>(0.10)<br>(0.025)<br>(0.352) | 30 | 70 | 180 |
| 27 (7) | Wescodyne (50) | Sodium formate (0.5) | " | NaH₂PO₄<br>Na₂HPO₄<br>Boric acid<br>NaCl | (0.023)<br>(0.10)<br>(0.025)<br>(0.352) | 25 | 60 | 240 |
| 28 (8) | Dermavan (50) | Sodium formate (0.5) | " | NaH₂PO₄<br>Na₂HPO₄<br>Boric acid<br>NaCl | (0.023)<br>(0.10)<br>(0.025)<br>(0.352) | 25 | 50 | 240 |
| 29 (9) | | Sodium formate (0.5) | " | NaH₂PO₄<br>Na₂HPO₄<br>Boric acid<br>NaCl | (0.023)<br>(0.10)<br>(0.025)<br>(0.352) | 35 | 50m | 240 |
| 30 (10) | Ioprep (50) | Sodium formate (0.5) | " | NaH₂PO₄<br>Na₂HPO₄<br>Boric acid<br>NaCl | (0.023)<br>(0.10)<br>(0.025)<br>(0.352) | 30 | 55 | 180 |
| 31 (11) | Ioprep (50) | Sodium formate (0.5) | " | NaH₂PO₄<br>Na₂HPO₄<br>Boric acid<br>NaCl | (0.023)<br>(0.10)<br>(0.025)<br>(0.352) | 20 | 50 | 180 |

NOTES
(1) Experiment carried out in presence of lens A, lens clear after 2 hours.
(2) Antorax (manufactured by General Aniline & Film Corporation) is believed to be an $I_2$/C0880 complex (C0880 is nonylphenoxy - polyoxyethylene ethanol) containing 20% of available iodine. Experiment carried out in presence of lens A, lens clear within 1 hour.
(3) Experiment carried out in presence of lens A, lens clear within 2 hours.
(4) Experiment carried out in presence of lens B, lens clear after 5 hours.
(5) Experiment carried out in presence of "Sauflor" lens (believed to contain at least 35% vinyl pyrrolidone,) lens still yellow after 24 hours.
(6) Wescodyne (manufactured by West Laboratories Inc.) is believed to comprise polyethoxypolyproxy ethanol/$I_2$ - 7.75% nonyl phenyl ether of propykne glycol/$I_2$ - 3.7%, water and acid to 100% and to contain 1.6% available iodine. Experiment carried out in presence of lens A, lens clear after 3 hours.
(7) Experiment carried out in presence of lens B, lens clear within 3 hours.
(8) Dermavan (manufactured by Evans Medical Limited) is stated to be a complex of iodine with 10% nonionic surface active agent and 10% industrial alcohol. Experiment carried out in presence of lens A, lens clear after 3 hours.
(9) Experiment carried out in presence of lens B, lens clear within 6 hours.
(10) Ioprep (manufactured by Johnson & Johnson) is believed to be an iodine complex with 10% of nonylphenoxy polyethylene glycol having 1% available iodine. Experiment carried out in presence of lens A, lens clear after 2 hours.
(11) Experiment carried out in presence of lens B, lens clear after 5 hours.

In experiments 21 and 22 the iodophors were diluted with 1% solutions of the respective surfactants and used in the iodophors. In experiments 23-33, the iodophors were diluted with distilled water.

In a further series of experiments the uptake of iodine from a PVP/$I_2$ solution into lenses and discs made of polymer A and polymer B.

To determine the uptake of iodine by the lenses, the colour change was observed spectrophotometrically.

The lenses were soaked in 50 ppm PVP/$I_2$ solutions and the iodine uptake by the lens measured. Discs of polymer A and polymer B that were cut from cast sheeting were also treated in this way. All readings were at 375 nm.

The polymer A samples reached a maximum value of about 2000 ppm $I_2$ of lens material in 2 hours. This is a concentration of about 40 times that of the soaking solution. There appeared to be no significant different between the polymer A lenses and discs once corrected for thickness. Polymer B lenses concentrated the iodine to such an extent that the colour produced was too strong to be measured after 30 minutes.

The release of iodine was observed under the same conditions as above, only a tablet containing 50 mg of sodium formate (as given in) Example 2) was added at zero time, this dissolved completely in about 15 minutes. Again, both polymer A and polymer B lenses and discs were used.

The iodine content of the PVP solution decreases to zero over 1 hour. The polymer A lenses and discs concentrate the iodine approximately eight times that of the starting solution, giving a maximum value of 400 ppm I which decreases to zero over 3 hours. The polymer B lenses and discs concentrate the iodine even further, approximately 20 times that of the original solution, approximately 2.5 times that of polymer A, giving a maximum value of 1,000 ppm decreasing to zero in about 8 hours. The polymer B film appears to release the iodine slightly faster than the polymer B lenses.

In further experiments the uptake of Iodine from the iodophor, namely Wescodyne and Antarox at 50 ppm available iodine levels into lenses made of polymers A and B was investigated. The experiments were carried out at ambient temperature and the iodine was induced by the addition of one tablet according to Example 2. The results are summarised in the following Table.

| Iodophor | Lens | Max. $I_2$ conc. (ppm) | Time taken to reduce max. $I_2$ concentration to | | |
|---|---|---|---|---|---|
| | | | 50% | 25% | Zero |
| Wescodyne | Polymer A | 200 | 30 | 40 | 80 |
| " | Polymer B | 1000 | 90 | 140 | >5 hours |
| Antarox | Polymer A | 180 | 50 | 20 | 40 |
| Antarox | Polymer B | 1800 | 55 | 130 | >5 hours |

1. The ocular response of the $PVPI_2$/formate system of Example 1 used with Polymer B and polymer A lenses has been assessed in a 28 day lens wearing study in 10 rabbits.

For each material, all eyes were fitted with lenses, which were worn 6 hours daily for 28 consecutive days. When removed from the eyes, all left lenses were sterilised in $PVP/I_2$/formate, and all right lenses were sterilised by boiling in saline.

No evidence of ocular irritation was seen with the slit lamp.

2. The ocular response of the above system has been assessed in a study using 12 volunteers (6 polymer A; 6 polymer B).

No evidence of ocular discomfort has been recorded in 3 polymer A and 3 polymer B wearers following 7 days use of the test solution.

In tests to establish the long term effect of the sterilization system according to the invention lenses made of polymers A and B were repeatedly immersed in solution made by combining the tablets of and sachets of Example 1 for a period of at least 4 hours. This procedure was repeated a total of 300 times and no appreciable change in weight or other characteristics were noted for the lenses.

We claim:

1. A method of sterilizing a contact lens formed of a hydrophilic polymer which comprises contacting the lens with an aqueous solution of an iodophor selected from the group consisting of complexes of iodine with hydrophilic polymers and nonionic surface active agents, said solution containing a sufficient quantity of an alkali metal salt of formic acid to reduce the available iodine level of the solution to substantially zero within a period of from 30 minutes to 8 hours at a temperature of from 20° to 25° C.; the reaction products of the iodophor and the alkali metal salt being non-toxic and a non-irritant.

2. A method as claimed in claim 1 in which the iodophor is a polyvinylpyrrolidone/iodine complex.

3. A method as claimed in claim 1 in which the solution contains sufficient alkali metal salt of formic acid to reduce the available iodine level of the solution to substantially zero within a period of from 1 to 4 hours at a temperature of from 20° to 25° C.

4. A method as claimed in claim 1 in which the sterilizing solution contains sufficient iodophor to give an initial available iodine concentration of at least 20 ppm.

5. A method as claimed in claim 4 in which the sterilizing solution contains sufficient iodophor to give an initial available iodine concentration of from 20 to 300 ppm.

6. A method as claimed in claim 5 in which the sterilizing solution contains sufficient iodophor to give an initial available iodine level of from 25 to 100 ppm.

7. A method as claimed in claim 1 in which the alkali metal salt is sodium formate.

8. A method as claimed in claim 1 in which the alkali metal salt of formic acid is present in an amount of from 10 to 800 moles per mole of iodine in the iodophor.

9. A method as claimed in claim 8 in which the alkali metal salt is present in an amount of from 100 to 400 moles per mole of iodine in the iodophor.

10. A method as claimed in claim 1 in which the solution also contains a buffering agent to give the solution a final pH of from 5 to 8.

11. A method as claimed in claim 10 in which the solution contains a buffering agent in an amount sufficient to give the solution a final pH of from 7 to 7.5.

12. A method as claimed in claim 1 in which the solution also contains a tonicity adjusting agent.

13. A two-part pack for the production of a sterilizing solution for treating a contact lens formed of a hydrophilic polymer comprising (a) an aqueous solution of an alkali metal salt of formic acid, and (b) a solid iodophor selected from the group consisting of complexes of iodine with hydrophilic polymers and nonionic surface active agents; the aqueous solution being such that when the solid iodophor is added to a predetermined quantity of the aqueous solution, the resulting sterilizing solution contains sufficient alkali metal salt to reduce the available iodine level of the sterilizing solution to substantially zero within a period of from 30 minutes to 8 hours at a temperature of from 20° to 25° C.; the reaction products of the iodophor and the alkali metal salt being non-toxic and a non-irritant.

14. A two-part pack as claimed in claim 13 in which the aqueous solution of alkali metal salt is contained in a sterilized package containing said predetermined quantity of reducing agent solution.

15. A two-part pack as claimed in claim 13 in which the quantity of aqueous solution of alkali metal salt contained in said container is more than said predetermined quantity of aqueous solution and the aqueous solution also contains an antibacterial preservative agent.

16. A two-part pack as claimed in claim 13 in which the solid iodophor also contains sodium chloride to render the final sterilizing solution isotonic.

17. A two-part pack as claimed in claim 13 in which the solid iodophor comprises from 2 to 30 mg of the iodophor.

18. A two-part pack as claimed in claim 17 in which the solid iodophor also contains sodium chloride.

19. A two-part pack for the production of a sterilizing solution for treating a contact lens formed of a hydrophilic polymer comprising (a) an aqueous solution of an iodophor selected from the group consisting of complexes of iodine with hydrophilic polymers and nonionic surface active agents and (b) a solid alkali metal salt of formic acid; the solid alkali metal salt and iodophor solution being such that when the solid alkali metal salt is added to a predetermined quantity of the iodophor solution, the resulting sterilizing solution contains sufficient alkali metal salt to reduce the available iodine level of the sterilizing solution to substantially zero within a period of from 30 minutes to 8 hours at a temperature of from 20° to 25° C.; the reaction products of the iodophor and the alkali metal salt being non-toxic and a non-irritant.

20. A two-part pack as claimed in claim 19 in which the solid alkali metal salt also contains a buffering agent in an amount sufficient to give the final sterilizing solution a pH of from 5 to 8.

21. A two-part pack as claimed in claim 19 in which the solid alkali metal salt also contains sodium chloride to render the final sterilizing solution isotonic.

22. A two-part pack as claimed in claim 19 in which the solid alkali metal salt is present in a quantity of from 20 to 300 mg.

23. A two-part pack as claimed in claim 22 in which the solid alkali metal salt also contains a buffering agent.

24. A two-part pack as claimed in claim 22 in which the solid alkali metal salt also contains sodium chloride.

25. A two-part pack for the production of a sterilizing solution for treating a contact lens formed of a hydrophilic polymer comprising (a) an aqueous solution of an alkali metal salt of formic acid, and (b) an aqueous solution of an iodophor selected from the group consisting of complexes of iodine with hydrophilic polymers and nonionic surface active agents; the iodophor and alkali metal salt solutions being such that when a predetermined quantity of the iodophor solution is added to a predetermined quantity of the alkali metal salt solution, the resulting sterilizing solution contains sufficient alkali metal salt to reduce the available iodine level of the sterilizing solution to substantially zero within a period of from 30 minutes to 8 hours at a temperature of from 20° to 25° C.; the reaction products of the iodophor and the alkali metal salt being non-toxic and a non-irritant.

26. A two-part pack as claimed in claim 25, in which the alkali metal salt solution is contained in a sterilized package containing said predetermined quantity of alkali metal salt solution.

27. A two-part pack as claimed in claim 25 in which the quantity of alkali metal salt solution contained in said container is more than said predetermined quantity of alkali metal salt solution and the alkali metal salt solution also contains an antibacterial preservative agent.

28. A two-part pack as claimed in claim 25, in which one or both of the alkali metal salt and iodophor solutions contain sodium chloride to render the final sterilizing solution isotonic.

29. A two-part pack as claimed in claim 25 in which one or both of the alkali metal salt and iodophor solutions contains a buffering agent.

30. A solid dosage unit form for the production of a sterilizing solution for treating a contact lens formed of a hydrophilic polymer comprising (a) a solid iodophor selected from the group consisting of complexes of iodine with hydrophilic polymers and nonionic surface active agents and (b) a solid alkali metal salt of formic acid, the iodophor and alkali metal salt being such that on dissolution in a predetermined quantity of water to form a sterilizing solution the resulting sterilizing solution contains a sufficient alkali metal salt to reduce the available iodine level of the sterilizing solution to substantially zero within a period of from 30 minutes to 8 hours at a temperature of from 20° to 25° C.

31. A solid dosage unit form as claimed in claim 30 containing from 2 to 30 mg of iodophor and from 20 to 300 mg of alkali metal salt.

32. A solid dosage unit form as claimed in claim 30 also containing sufficient sodium chloride to render the sterilizing solution isotonic.

33. A solid dosage unit form as claimed in claim 30 also containing sufficient of a buffer to give the sterilizing solution a pH of from 5.0 to 8.0.

34. A two-part pack for the production of a sterilizing solution for treating a contact lens formed of a hydrophilic polymer comprising (i) a solid dosage unit form comprising (a) a solid iodophor selected from the group consisting of complexes of iodine with hydrophilic polymers and nonionic surface active agents and (b) a solid alkali metal salt of formic acid and (ii) water; the iodophor and alkali metal salt being such that on dissolution in a predetermined quantity of water to form a sterilizing solution the resulting sterilizing solution contains sufficient alkali metal salt to reduce the available iodine level of the sterilizing solution to substantially zero within a period of from 30 minutes to 8 hours at a temperature of from 20° to 25° C.

35. A two-part pack as claimed in claim 34 in which the water is contained in a sterilized package containing said predetermined quantity of water.

36. A two-part pack as claimed in claim 34 in which the quantity of water contained in said container is greater than the said predetermined quantity and the water also contains an antibacterial preservative agent.

37. A method of sterilizing a contact lens formed of a hydrophilic polymer which comprises contacting the lens with an aqueous solution of an iodophor selected from the group consisting of complexes of iodine with hydrophilic polymers and nonionic surface active agents containing sufficient iodophor to give an initial available iodine concentration of at least 20 ppm, said solution containing an alkali metal salt of formic acid in an amount of from 10 to 800 moles per mole of available iodine in the iodophor.

38. A method as claimed in claim 37 in which the iodophor is a polyvinylpyrrolidone/iodine complex.

39. A method as claimed in claim 37 in which the sterilizing solution contains sufficient iodophor to give an initial available iodine concentration of from 20 to 300 ppm.

40. A method as claimed in claim 39 in which the sterilizing solution contains sufficient iodophor to give an initial available iodine level of from 25 to 100 ppm.

41. A method as claimed in claim 37 in which the alkali metal salt is sodium formate.

42. A method as claimed in claim 37 in which the alkali metal salt is present in an amount of from 100 to 400 moles per mole of iodine in the iodophor.

43. A method as claimed in claim 37 in which the solution also contains a buffering agent to give the solution a final pH of from 5 to 8.

44. A method as claimed in claim 37 in which the solution contains a buffering agent in an amount sufficient to give the solution a final pH of from 7 to 7.5.

45. A method as claimed in claim 37 in which the solution also contains a tonicity adjusting agent.

* * * * *